United States Patent
Howell et al.

(10) Patent No.: US 9,738,773 B2
(45) Date of Patent: Aug. 22, 2017

(54) FLAME RETARDANTS FROM RENEWABLE RESOURCES

(71) Applicant: Central Michigan University, Mount Pleasant, MI (US)

(72) Inventors: Bob A. Howell, Mount Pleasant, MI (US); Yoseph G. Daniel, Mount Pleasant, MI (US)

(73) Assignee: Central Michigan University, Mount Pleasant, MI (US)

( * ) Notice: Subject to any disclaimer, the term of this patent is extended or adjusted under 35 U.S.C. 154(b) by 0 days.

(21) Appl. No.: 14/821,147

(22) Filed: Aug. 7, 2015

(65) Prior Publication Data

US 2016/0046792 A1    Feb. 18, 2016

Related U.S. Application Data

(60) Provisional application No. 62/035,041, filed on Aug. 8, 2014.

(51) Int. Cl.

| | |
|---|---|
| *C08J 3/00* | (2006.01) |
| *C07D 327/00* | (2006.01) |
| *C07D 321/00* | (2006.01) |
| *C07F 9/02* | (2006.01) |
| *C07C 315/00* | (2006.01) |
| *C07C 317/00* | (2006.01) |
| *C08K 5/529* | (2006.01) |
| *C09K 21/12* | (2006.01) |
| *C07F 9/6561* | (2006.01) |
| *C08K 5/5377* | (2006.01) |
| *C07F 9/6571* | (2006.01) |

(52) U.S. Cl.
CPC ............ *C08K 5/529* (2013.01); *C07F 9/6561* (2013.01); *C07F 9/657181* (2013.01); *C08K 5/5377* (2013.01); *C09K 21/12* (2013.01)

(58) Field of Classification Search
CPC ...... C08K 5/529; C08K 5/5377; C09K 21/12; C07F 9/6561; C07F 9/657181
USPC ......... 523/451, 1; 524/1; 549/5, 222, 1, 200, 549/218; 540/1; 568/8, 17, 18, 27, 37, 568/75, 77, 300
See application file for complete search history.

(56) References Cited

U.S. PATENT DOCUMENTS

| | | |
|---|---|---|
| 2009/0220662 A1 | 9/2009 | Tachdjian et al. |
| 2010/0249189 A1* | 9/2010 | Almirante ............ C07D 493/04 514/321 |
| 2013/0032056 A1 | 2/2013 | Goredema et al. |
| 2013/0296584 A1 | 11/2013 | Howard et al. |
| 2014/0088226 A1 | 3/2014 | Gevers et al. |

OTHER PUBLICATIONS

Hu et al., "Synthesis and phase behavior of side-chain cholesteric liquid-crystalline elastomers derived form a chiral crosslinking agent", Jun. 2, 2005, Reactive & Functional Polymers, vol. 64, p. 1-11.*

(Continued)

*Primary Examiner* — David Karst
(74) *Attorney, Agent, or Firm* — Michael Best & Friedrich LLP

(57) ABSTRACT

Among other things the invention provides novel flame-retardant compounds useful for increasing the flame retardance of polymers.

19 Claims, 20 Drawing Sheets

Isosorbide Di[14-(diphenylphosphato)-12-thiatetradecanoate] [DPPA]

Isosorbide Di[14-(diethylphosphato)-12-thiatetradecanoate] [DPPE]

Isosorbide Di[14-(diphosphinato)-12-thiatetradecanoate] [DPPI]

Isosorbide Di(14-dopyl-12-thiatetradecanoate) [DPPD]

(56) References Cited

OTHER PUBLICATIONS

Zenner et al., "Polyurethanes from Isosorbide-Based Diisocyanates", Jun. 11, 2013, ChemSusChem, vol. 6, p. 1182-1185.*

Howell, et al., "Thermal degradation of phosphorus esters derived from isosorbide and 10-undecenoic Acid," Journal of Thermal Analysis and Calorimetry (2015) 121(1):411-419.

International Search Report and Written Opinion for Application No. PCT/US2015/44261 dated Nov. 19, 2015 (9 pages).

* cited by examiner

Isosorbide Di[14-(diphenylphosphato)-12-thiatetradecanoate] [DPPA]

Isosorbide Di[14-(diethylphosphato)-12-thiatetradecanoate] [DPPE]

Isosorbide Di[14-(diphosphinato)-12-thiatetradecanoate] [DPPI]

Isosorbide Di(14-dopyl-12-thiatetradecanoate) [DPPD]

Preparation of Isosorbide Di(undec-10-enoate)

Scheme 1

Scheme 2

FLAME RETARDANTS FROM RENEWABLE RESOURCES

CROSS-REFERENCE TO RELATED APPLICATIONS

The present application claims priority to U.S. Application Ser. No. 62/035,041, filed Aug. 8, 2014, which is incorporated herein by reference.

BACKGROUND OF THE INVENTION

The production of polymeric materials, now approaching three million tons per year, has had a profound effect on modern society. The development of polymeric materials since World War II is largely responsible for the high standard of living enjoyed by most people of the developed world. In general, polymeric materials are flammable and must be flame retarded for most applications. Flame retardance may be imparted in a number of ways, including introducing a flame retarding additive during polymer processing.

Organohalogen compounds, particularly brominated aryl ethers, are effective gas-phase flame retardants which are readily available at low cost. However, when released into the environment these compounds do not readily undergo degradation, tend to bioaccumulate, and may pose human health risks. For this reason, these compounds are being removed from the market. New non-toxic flame retardants are needed.

DETAILED DESCRIPTION OF THE INVENTION

Figure 1:
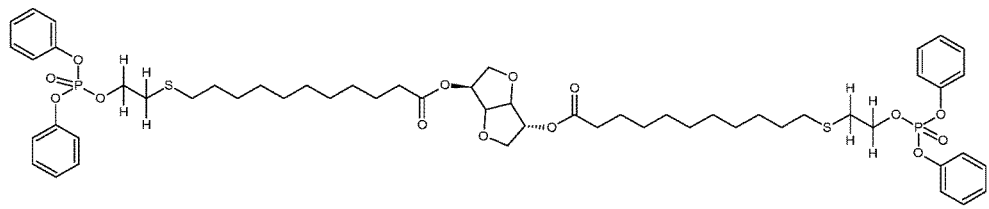
FIG. 1 illustrates a number of compounds according to the present invention.
Figure 1:
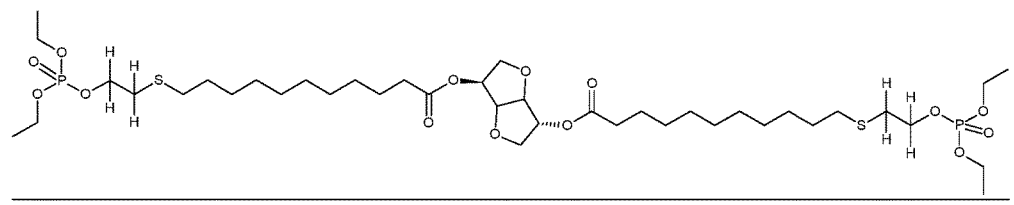
Figure 1:
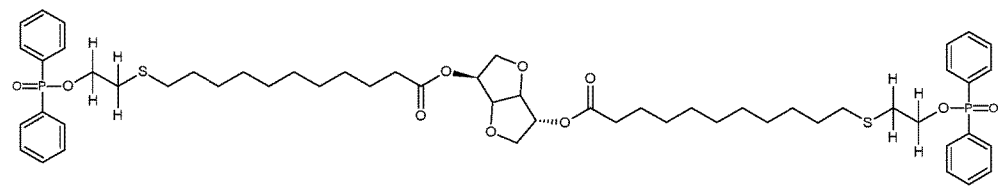
Figure 1:
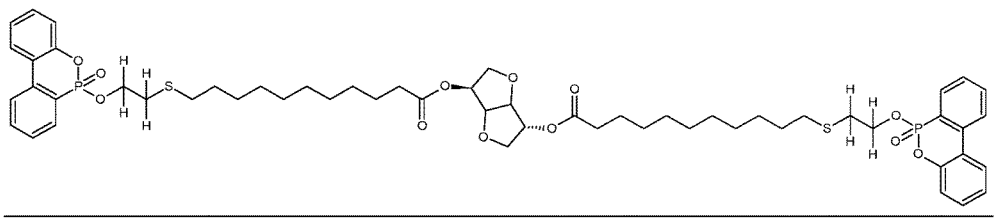

There is increasing interest in generating polymer additives from renewable biomaterials. In particular, flame retardants produced from biomaterials offer several attractive advantages over more traditional materials, e.g. the necessary starting materials are sustainably available from plant source and the resulting flame amendments are generally nontoxic and biodegradable.

Among other things, the present invention provides compounds, synthetic methods and methods of use for flame retardants from renewable resources such as isosorbide and 10-undecenoic acid. In some embodiments, these flame retardants are non-volatile and/or non-migratory.

Definitions

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, thioxo, oxo, and cyano. Additionally, the suitable indicated groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)

—O$_2$RR, —P(=O)O$_2$RR, —P(=O)(O)$_2$, —P(=O)(OH)$_2$, —C(=O)R, —C(=O)X, —C(S)R, —C(O)OR, —C(O)O, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings or from 3 to 7 carbon atoms or from 5 to 6 carbon atoms. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" or "Ar" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms or from 6 to 20 carbon atoms or from 6 to 12 carbon atoms or from 6 to 10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2 to 20 carbon atoms in addition to the one or more heteroatoms or 5 to 15 carbon atoms in addition to the one or more heteroatoms or 4 to 10 carbon atoms in addition to the one or more heteroatoms. Typical heteroaryl groups contain 6 to 30 ring atoms or 6 to 20 ring atoms or 6 to 12 ring atoms or 6 to 10 ring atoms. Suitably the heteroaryl contains up to 4 heteroatoms or 3 heteroatoms or 2 heteroatoms.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl.

In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or (C$_1$-C$_6$) alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. Typical heteroaryl groups contain 2 to 20 carbon atoms in addition to the one or more heteroatoms or 5 to 15 carbon atoms in addition to the one or more heteroatoms or 4 to 10 carbon atoms in addition to the one or more heteroatoms. Typical heteroaryl groups contain 6 to 30 ring atoms or 6 to 20 ring atoms or 6 to 12 ring atoms or 6 to 10 ring atoms. Suitably the heterocycle contains up to 4 heteroatoms. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted".

The term "alkylamino" refers to —NR$_2$, wherein at least one R is alkyl and the second R is alkyl or hydrogen.

The term "acylamino" refers to N(R)C(=O)R, wherein each R is independently hydrogen, alkyl, or aryl.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

Compounds

The invention provides compounds according to Formula (I):

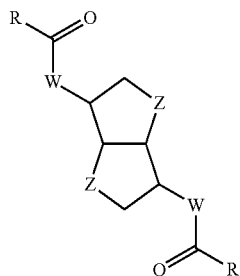

wherein
each Z is independently selected from O, N and S;
each W is independently selected from O and N;
R is -A-X;
A is an alkylene chain which may be substituted or interrupted by one or more heteroatoms selected from O, N, and S;
X is selected from —CH=$CH_2$, —S($CR^1R^2$)$_m$—Y, —S(O)($CR^1R^2$)$_m$—Y, —S(O)$_2$($CR^1R^2$)$_m$—Y, —Y, or halogen;
Y is selected from —P(O)($R^3$)$_2$, —P(O)($OR^4$)$_2$, —P(O)($OR^4$)$R^3$; —OP(O)($R^3$)$_2$, —OP(O)($OR^4$)$_2$, —OP(O)($OR^4$)$R^3$ or

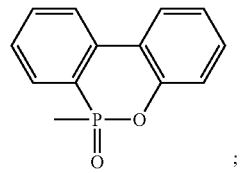

each $R^1$ and $R^2$ is independently selected from the group consisting of H, hydroxyl, and halogen;
each $R^3$ and $R^4$ is independently selected from $C_{1-10}$ alkyl or aryl;

n is an integer from 2 to 20; and
m is an integer from 1 to 10.

In some embodiments, the alkylene chain contains from 2 to 20 member atoms. In some embodiments, the alkylene chain contains 1-5 heteroatoms. In some embodiments, -A-X is ($CR^1R^2$)$_n$—X, wherein each $R^1$ and $R^2$ is independently selected from the group consisting of H, hydroxyl, and halogen. In some embodiments, n is 2 to 10. In some embodiments, n is 4-8. In some embodiments, $R^3$ and/or $R^4$ is $C_{1-4}$ alkyl. In some embodiments, m is 1 to 2. In some embodiments, W is O. In some embodiments, Z is O.

Suitable compounds according to Formula (I) include those shown in FIG. 1.

Synthesis of Compounds

Compounds described herein may be synthesized using a variety of methods. For example, the dietherdiol is esterified with an unsaturated hydrocarbon (or alkylene chain). That product is then reacted with a bromination reagent or a phosphorus containing reagent to obtain the desired flame retardant.

Figure 23:
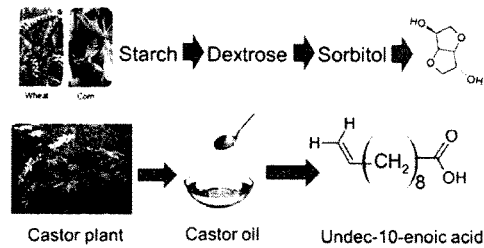
FIG. 23 shows Scheme 1 illustrating the generation of isosorbide and 10-undecenoic acid from biosurces.

Isosorbide is a dietherdiol which may be conveniently produced from starch by hydrolysis to glucose followed by aldehyde reduction and double dehydration. 10-undecenoic acid may be derived from a component of castor oil. Castor oil is a non-edible oil widely used for the production of biodiesel. Its use as a feedstock does not impact the world food supply. The production of both isosorbide and 10-undecenoic acid is illustrated in Scheme 1 (FIG. 23).

Figure 24:
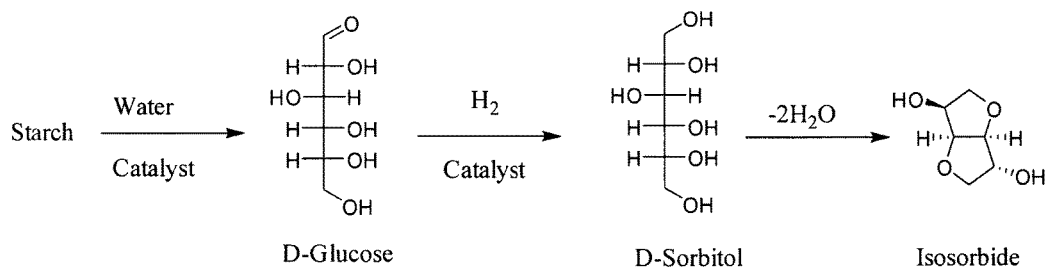
FIG. 24 shows Scheme 2 illustrating the conversion of glucose to isosorbide.

Hydrolysis of starch, followed by aldehyde reduction and double dehydration affords isosorbide as shown in Scheme 2 (FIG. 24). Isosorbide is also commercially available in good purity.

Glucose may also be obtained from cellulose (crop residue, wood waste, switch grass, etc.). Cellulose is abundantly available and is not a food source.

10-Undecenoic (undecyclenic) acid may be generated either by pyrolysis of castor oil directly or pyrolysis of ricinoleic acid, a castor oil constituent (Scheme 3).

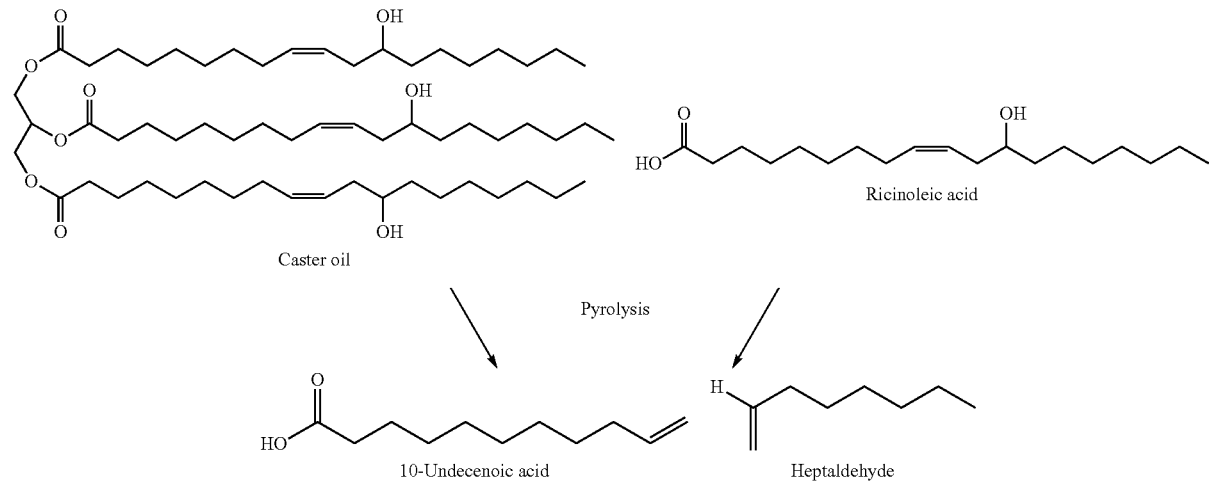

Scheme 3. Generation of 10-Undecenoic Acid.

Esterification of isosorbide with 10-undecenoic acid can be accomplished either directly or via the acid chloride (Scheme 4). Yields of diester are comparable using either approach. The crude ester may be conveniently purified by silica gel chromatography using ethyl acetate/hexane as eluant. The unsaturated end-groups of the diester provide suitable functionality for conversion to a variety of phosphorus-containing compounds. Many of these display good flame retardant activity.

Scheme 4. Preparation of Isosorbide Di(undec-10-enoate).

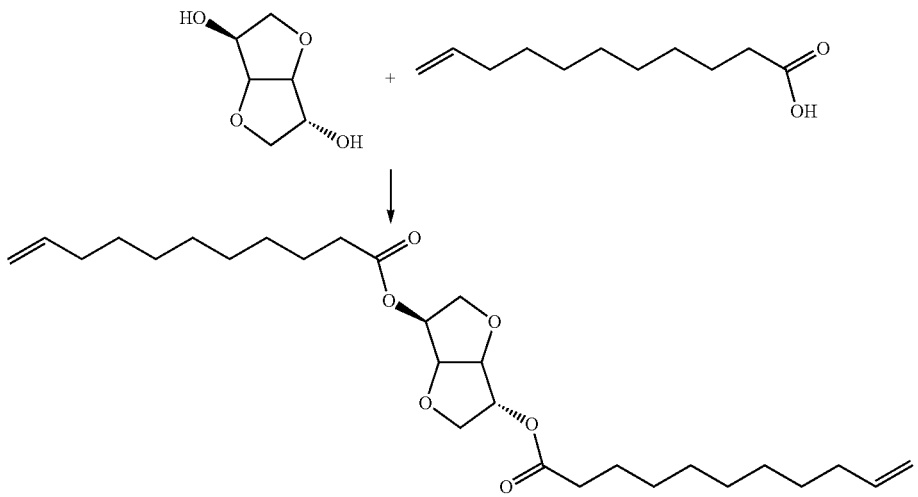

For example, isosorbide is esterified with 10-undececnoic acid to give the corresponding ester with two unsaturations. Bromination then yields a tetrabromo derivative, isosorbide di(10,11-dibromoundecanoate). The level of bromination can be adjusted by esterifying with either linoleic acid or linolenic acid. Exemplary syntheses are generalized in FIGS. 8-11.

As can be appreciated by the skilled artisan, alternative methods of synthesizing the compounds of the present invention will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Methods of Use

The compounds of the present invention are suitable used as flame retardants. In some embodiments, the compounds of the present invention are used to increase the thermal stability of a polymer. In some embodiments, the compounds of the present invention are used to increase the maximum thermal degradation temperature of a polymer. In embodiments, the maximum thermal degradation temperature of a modified polymer may be greater than about 200° C. or greater than about 250° C. or greater than about 275° C. or greater than about 300° C. or greater than about 325° C. or greater than about 350° C. or greater than about 400° C.

For example, the compounds of the present invention may be used as an additive during polymer processing. In some embodiments, at least about 10% by weight is added, or at least about 15%, or at least about 20%, or at least about 25%, or at least about 30% or at least about 35%, or at least about 40%, or at least about 45% or at least about 50%. In some embodiments, less than about 60% by weight is added, or less than about 50%, or less than about 45%, or less than about 40%, or less than about 35%, or less than about 30%, or less than about 25%, or less than about 20%, or less than about 15%, or less than about 10%.

In some embodiments, sufficient additive is added to obtain a loading of at least about 0.01% phosphorus, or at least about 0.05%, or at least about 0.1%, or at least about 0.5%, or at least about 1% or at least about 1.5%, or at least about 2%, or at least about 2.5% or at least about 3%, or at least about 4%, or at least about 5%, or at least about 8%, or at least about 10%. In some embodiments, sufficient additive is added to obtain a loading of less than about 15% phosphorus, or less than about 10%, or less than about 8%, or less than about 5%, or less than about 4%, or less than about 3%, or less than about 2.5%, or less than about 2%, or less than about 1.5%, or less than about 1%, or less than about 0.5%, or less than about 0.1%, or less than about 0.05% or less than about 0.01%.

The invention is further described by the following non-limiting examples.

EXAMPLES

Common solvents and reagents were obtained from ThermoFisher Scientific or the Aldrich Chemical Company. Isosorbide 10-undecenoic acid and 2-ethyl-4-methylimidazole were from the Aldrich Chemical Company. DEGBA was generously supplied by the Dow Chemical Company.

Instrumentation and Characterization

Infrared spectra were obtained by ATR using a Thermo Scientific Nicolet 380 FT-IR spectrophotometer. Absorptions were recorded in wavenumbers ($cm^{-1}$) and absorption intensities were classified in the usual fashion as very weak (vw), weak (w), medium (m), strong (s), and very strong (vs) relative to the strongest band in the spectrum. Nuclear magnetic resonance (NMR) spectra were obtained using a 5-15% solution in deuterochloroform using a Varian Mercury 300 MHz or a INOVA 500 MHz spectrometer. Proton and carbon chemical shifts are reported in a parts-per-million (δ) with respect to tetramethylsilane (TMS) as an internal reference (δ=0.00). Mass spectra were obtained using electrospray ionization (ESI/MS) with a Waters Associates LCT Premier XE instrument interfaced with a Waters Acquity Ultra Performance Liquid Chromatograph or matrix assisted laser desorption time of flight mass spectrometry (MALDI-TOFMS) and a Bruker Daltonics Autoflex unit. A MALDI matrix was determined experimentally but was most usually 2,5-dihydrobenzoic acid. Thermal transitions were determined by differential scanning calorimetry (DSC) using a TA instruments Q2000 instrument. Samples, contained in standard aluminum pans, were analyzed at heating rate of 5 or 10° C. min$^{-1}$ Thermogravimetry was performed using a TA instruments Q500 instrument. Typically, a heating rate of 5° C. min$^{-1}$ was used. Samples (4-10 mg) were contained in a platinum pan. The sample compartment was purged with dry nitrogen at 50 cm$^3$ min$^{-1}$ during analysis. TA Universal Analysis software was used for data analysis. Pyrolysis combustion flow calorimetry (PCFC) was conducted using a FireTesting Technology microcalorimeter.

Example 1

Synthesis of Isosorbide Di(undec-10-enoate)

Into a 250-ml, round-bottomed flask fitted with a magnetic stirring bar and a Dean-Stark trap bearing a Liebig condenser was placed 20.10 g (0.134 mol) of isosorbide, 55.31 g (0.267 mol) of undec-10-enoic acid and 0.52 g (2.73 mmol) of toluenesulfonic acid monohydrate in 125 ml of toluene. The solution was stirred at solvent reflux with water being continuously removed as the toluene azeotrope for 12 hr. At this point no further water was being collected. The mixture was allowed to cool to room temperature and washed, successively, with two 50-ml portions of saturated aqueous sodium bicarbonate solution and 50 ml of saturated aqueous sodium chloride solution. The solution was dried over anhydrous sodium sulfate and the solvent was removed by rotary evaporation at reduced pressure to afford 59.85 g of crude product as a pale yellow viscous oil. This material was subjected to column chromatography using SilaCycle P60 240 mesh silica gel and hexane/ethyl acetate (90:10) as eluent to provide 35.82 g (55.8% yield) of isosorbide di(undec-10-enoate) as a colorless oil: ir(cm$^{-1}$, ATR) 3076 (m), $C_{sp2}$—H, 2910 (s), 2850 (s), $C_{sp3}$—H, 1740 (vs), C=O, 1643 (m), C=C, 1060 (s), C—O; $^1$H NMR (δ, CDCl$_3$) 1.28 (m), 1.61 (m), 2.02 (m), 2.33 (m), aliphatic protons of the ester, 3.77 (m), 3.94 (m), 4.46 (m), 4.82 (m), 4.94 (m), 5.11 (m), isosorbide protons, 5.17, 5.78, 5.82, ABX pattern, olefinic protons; $^{13}$C NMR (δ, CDCl$_3$) 24.8, 28.8, 29.0, 33.7, 33.9, 34.1, aliphatic carbon atoms, 70.3, 73.4, 73.7, 76.6, 80.7, 85.9, isosorbide carbon atoms, 114.1, 139.1, olefinic carbon atoms, 172.8, 173.1, carbonyl carbon atoms.

Example 2

Preparation of Test Specimen

A phosphorus compound was dissolved in) at the level required to incorporate the desired loading of phosphorus. Hardener, 2-ethyl-4-methylimidazole, was added (0.5 part hardener to 1 part DGEBA). The mixture was stirred vigorously for three minutes and poured into warm Teflon coated aluminum molds of appropriate dimensions. The material was cured at 90° C. for 1 hour and then at 130° C. for 2 hours. The samples were allowed to cool slowly to room temperature.

Example 3

Properties of Phosphorus Esters

Figure 2:
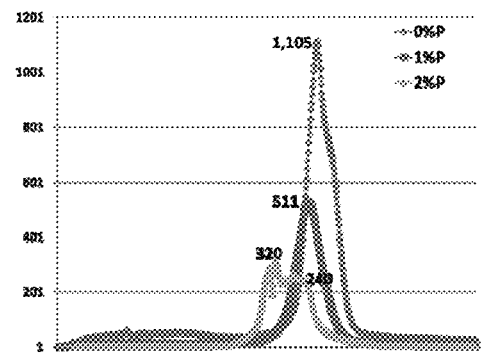
FIG. 2 shows PCFC for Epoxy Resin Containing a Starch/Castor Oil Derived Phosphorus Compound.

The flame retardants of the present invention suppress the peak heat release rate (PHRR) for the combustion of DGEBA epoxy (FIG. 2). Incorporation of sufficient additive to provide a loading of 1% phosphorus reduces PHHR by half. The presence of 2% phosphorus reduces the PHHR to 33% of that for the epoxy with no flame retardant present.

Example 4

Thermal Degradation Behavior of Phosphorus Esters

Figure 3:
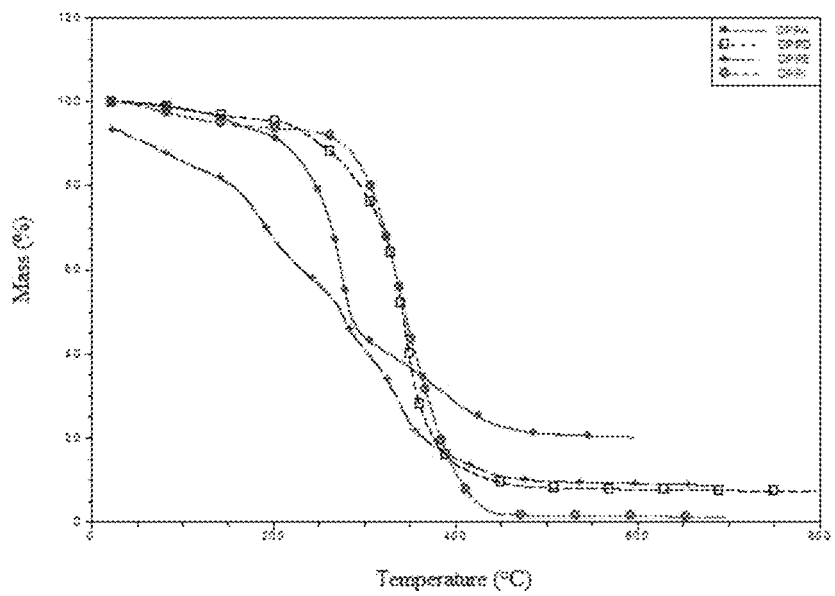
FIG. 3 shows thermal degradation of phosphorus esters, DPPA, DPPE, DPPI, and DPPD, as a function of temperature.

The thermal degradation behavior of the phosphorus esters has been examined using thermogravimetry and infrared spectroscopy. Decomposition of the esters as a function of temperature is displayed in FIG. 3.

As may be seen DPPE is the least stable and decomposes over a relatively wide temperature range and in several steps. DPPI and DPPD are the most stable. Details of the decomposition of all the esters are provided in Table 1.

TABLE 1

Thermal Decomposition of Phosphorus Esters, DPPA, DPPE, DPPI, and DPPD.

| Compound | Onset Temperature (° C.)[a] | Maximum Decomposition Temperature (° C.)[b] | Decomposition Residue (%)[c] |
|---|---|---|---|
| DPPA | 262 | 293 | 13 |
| DPPE | 144 | 190 | 16 |
| DPPI | 278 | 337 | 8 |
| DPPD | 316 | 345 | 12 |

[a]Extrapolated onset temperature from the TGA derivative plot.
[b]Temperature of maximum degradation rate.
[c]Residue at 600° C. as a percentage of the initial sample mass.

Figure 4:
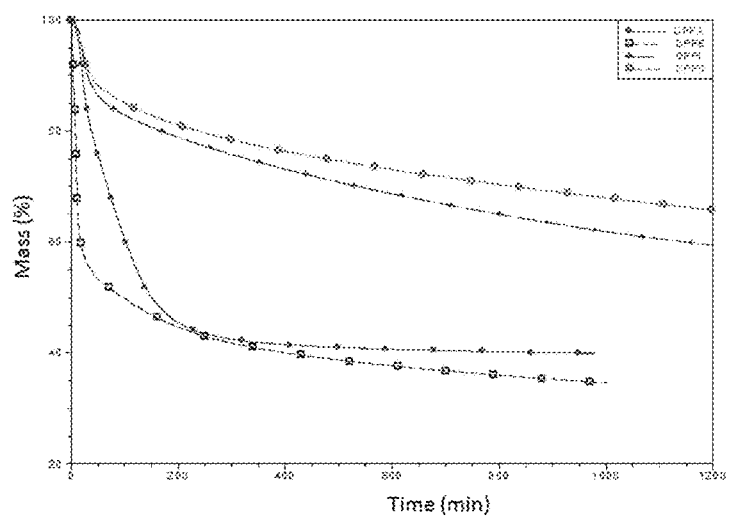
FIG. 4 shows thermal degradation of phosphorus Esters, DPPA, DPPE, DPPI, and DPPD at 200° C.

Isothermal decomposition at 200° C. is illustrated in FIG. 4. Two of these, DPPE and DPPA, undergo rapid initial mass loss (about half of the initial sample mass is lost over the first three hours) to afford a residue stable at 200° C.

DPPI and DPPD degrade less readily with DPPD being the most stable at 200° C. (approximately 20% of the initial sample mass is lost over the first three hours). The mass loss is detailed in Table 2.

TABLE 2

Thermal Degradation of Phosphorus Esters at 200° C.

| Compound | Residue at 4 hours (%)* | Residue at 10 hours (%)* |
|---|---|---|
| DPPA | 44 | 41 |
| DPPE | 43 | 38 |
| DPPI | 78 | 69 |
| DPPD | 80 | 73 |

*Residue as a percentage of the initial sample mass.

The mass loss would suggest that both DPPE and DPPA degrade by rapid loss of both phosphate groups probably by elimination of the corresponding phosphorus acid. The other two may degrade in the same way but at a much slower rate.

Figure 5:
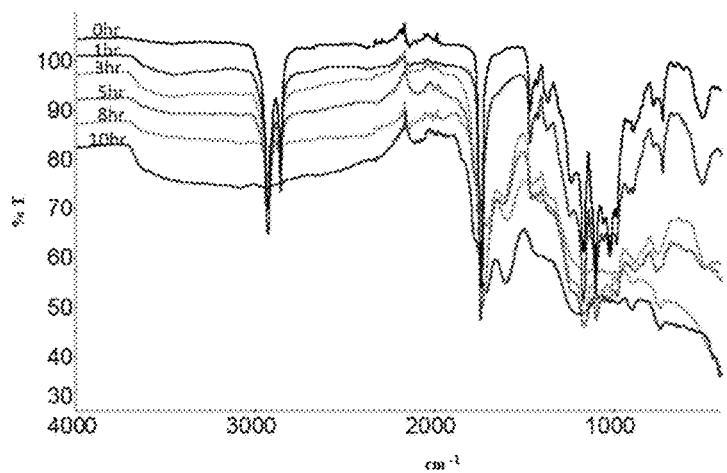
FIG. 5 shows thermal degradation of DPPE at 260° C.

The thermal degradation of the phosphate esters was also monitored using infrared spectroscopy. Samples of the ester were placed in an oven maintained at 260° C. Periodically, a sample was removed for analysis. Results for the degradation of DPPE are shown in FIG. 5. As degradation proceeds several changes in the infrared spectrum become apparent.

Most of these occur in the molecular vibration region, 1400-700 cm$^1$, but the most informative is the growth of a broad hydroxyl band, 3500-2500 cm-1. Without wishing to be bound by theory, this is probably reflective of the formation of a phosphorus acid (Scheme 5.)

Scheme 5. Proposed Degradation Pathway for DPPE.

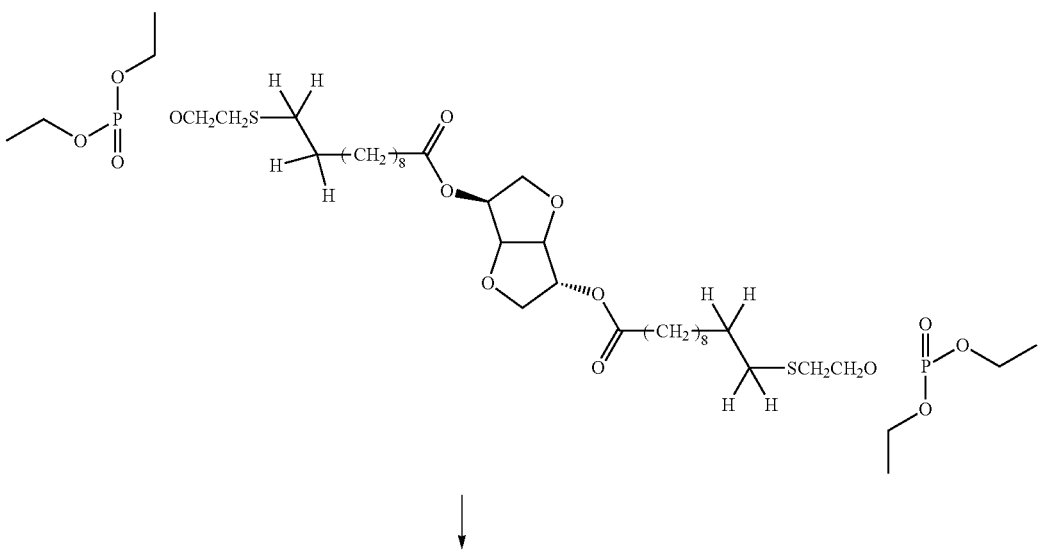

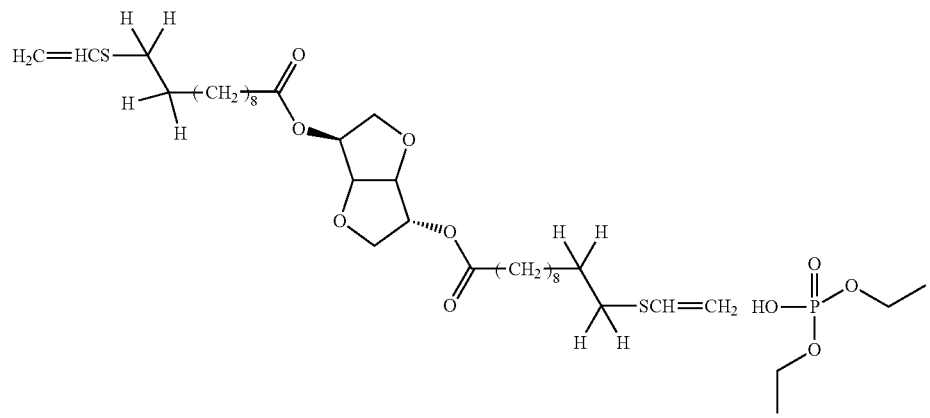

Figure 6:
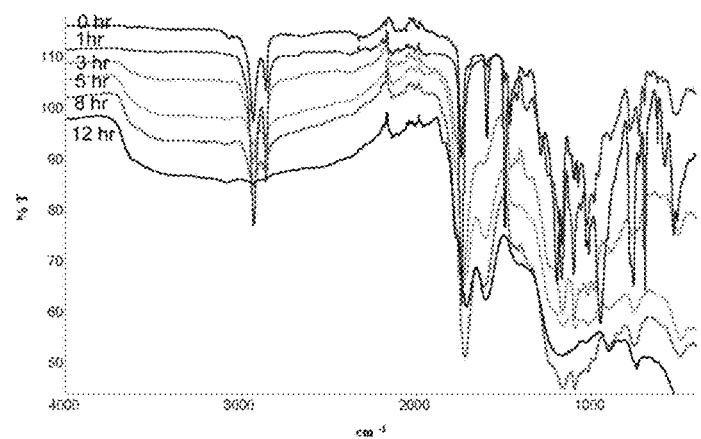
FIG. 6 shows thermal degradation of DPPA at 260° C.

Changes in the infrared spectrum of DPPA which accompany its degradation are shown in FIG. 6. The changes are similar to those observed for the degradation of DPPE and probably reflect a comparable elimination of a phosphorus acid.

Figure 7:
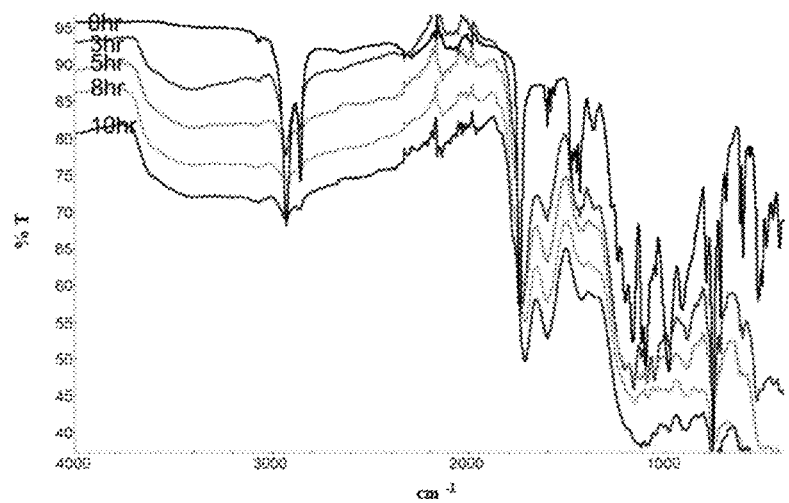
FIG. 7 shows thermal degradation of DPPD at 260° C.
Figure 8:
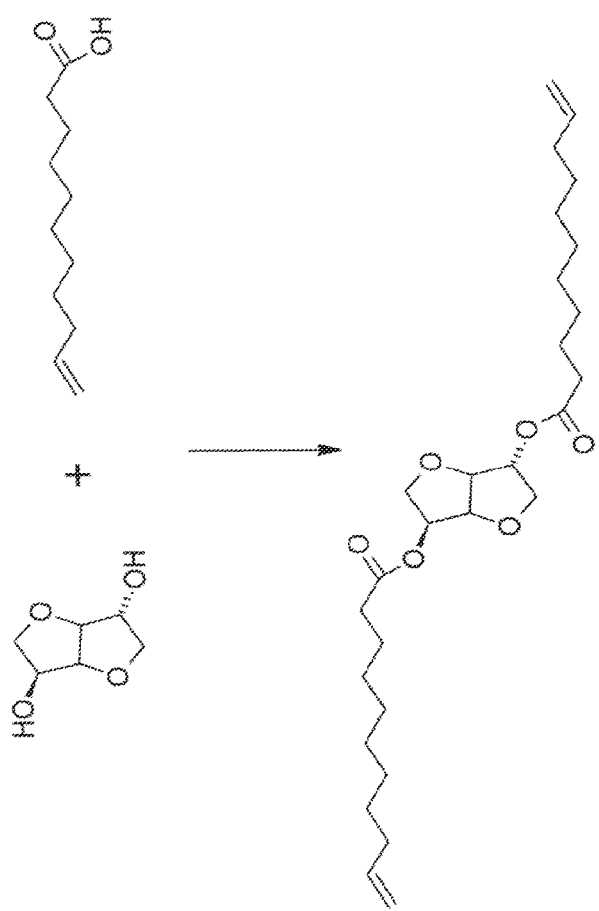
FIG. 8 shows a synthetic scheme for the compounds of the present invention.
Figure 9:
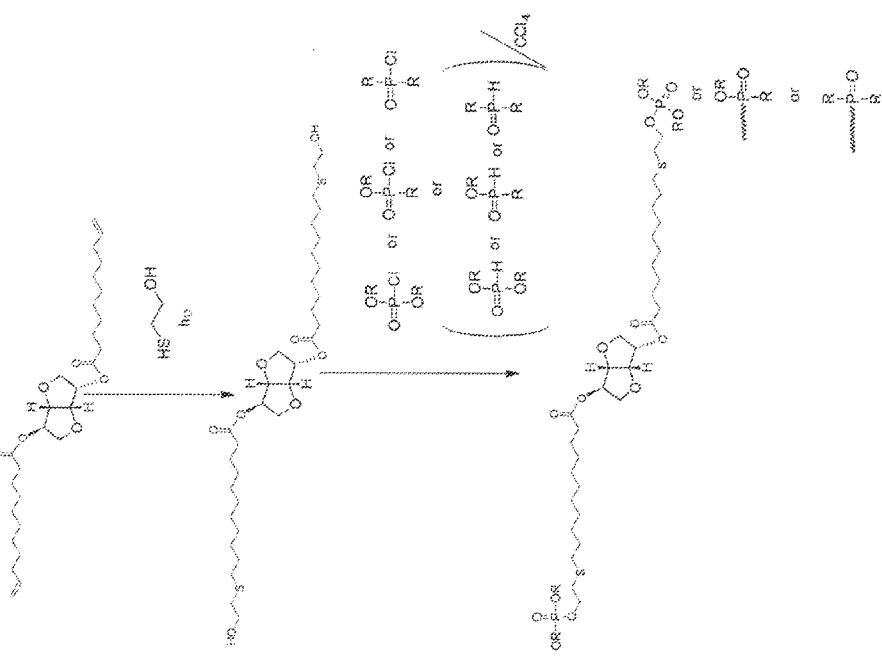
FIG. 9 shows a synthetic scheme for the compounds of the present invention.
Figure 10:
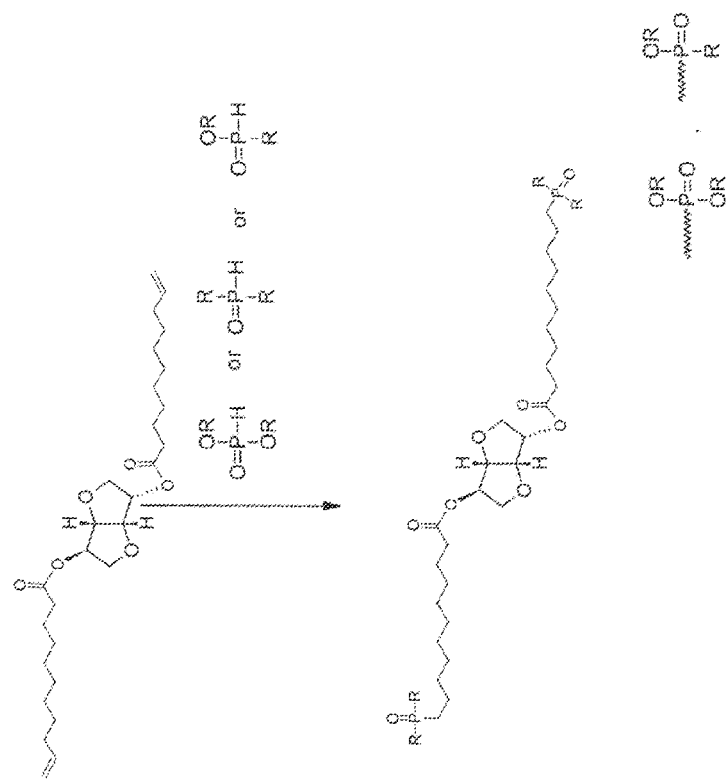
FIG. 10 shows a synthetic scheme for the compounds of the present invention.
Figure 11:
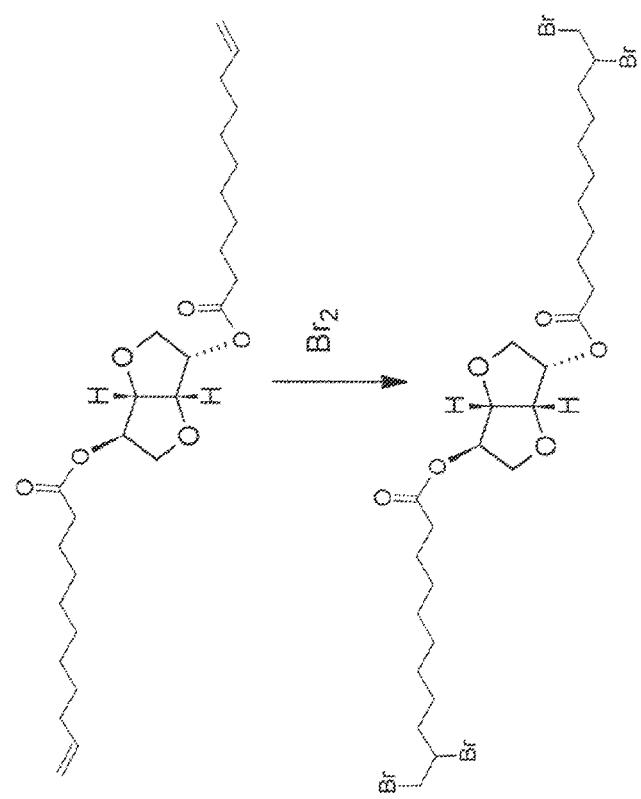
FIG. 11 shows a synthetic scheme for the compounds of the present invention.
Figure 12:
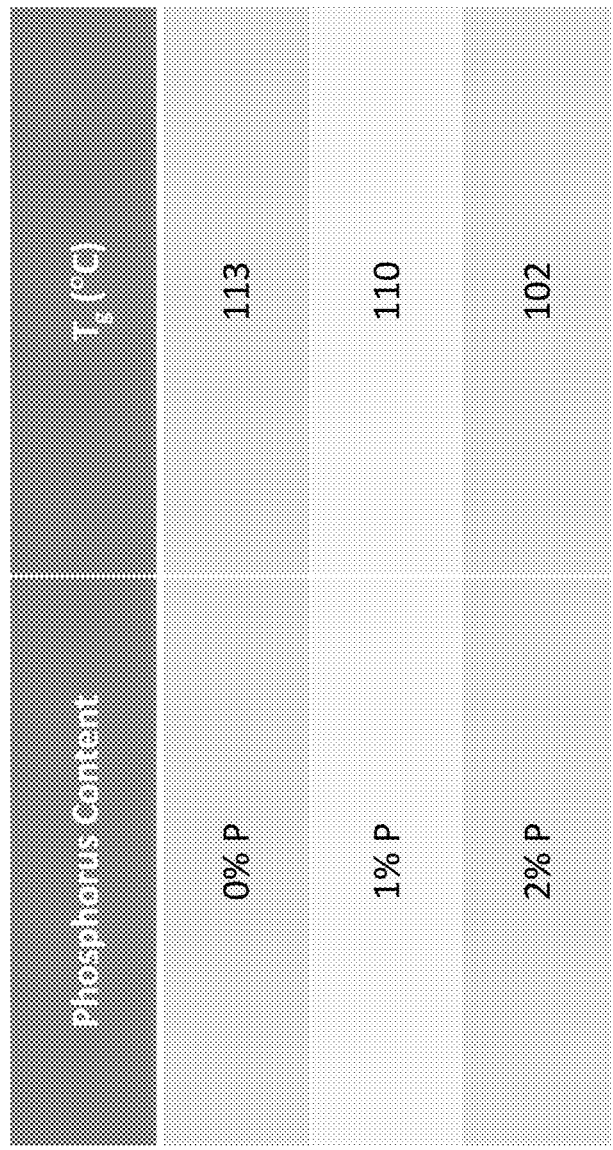
FIG. 12 shows glass transition temperatures for DGEBA epoxy containing DPPD.
Figure 13:
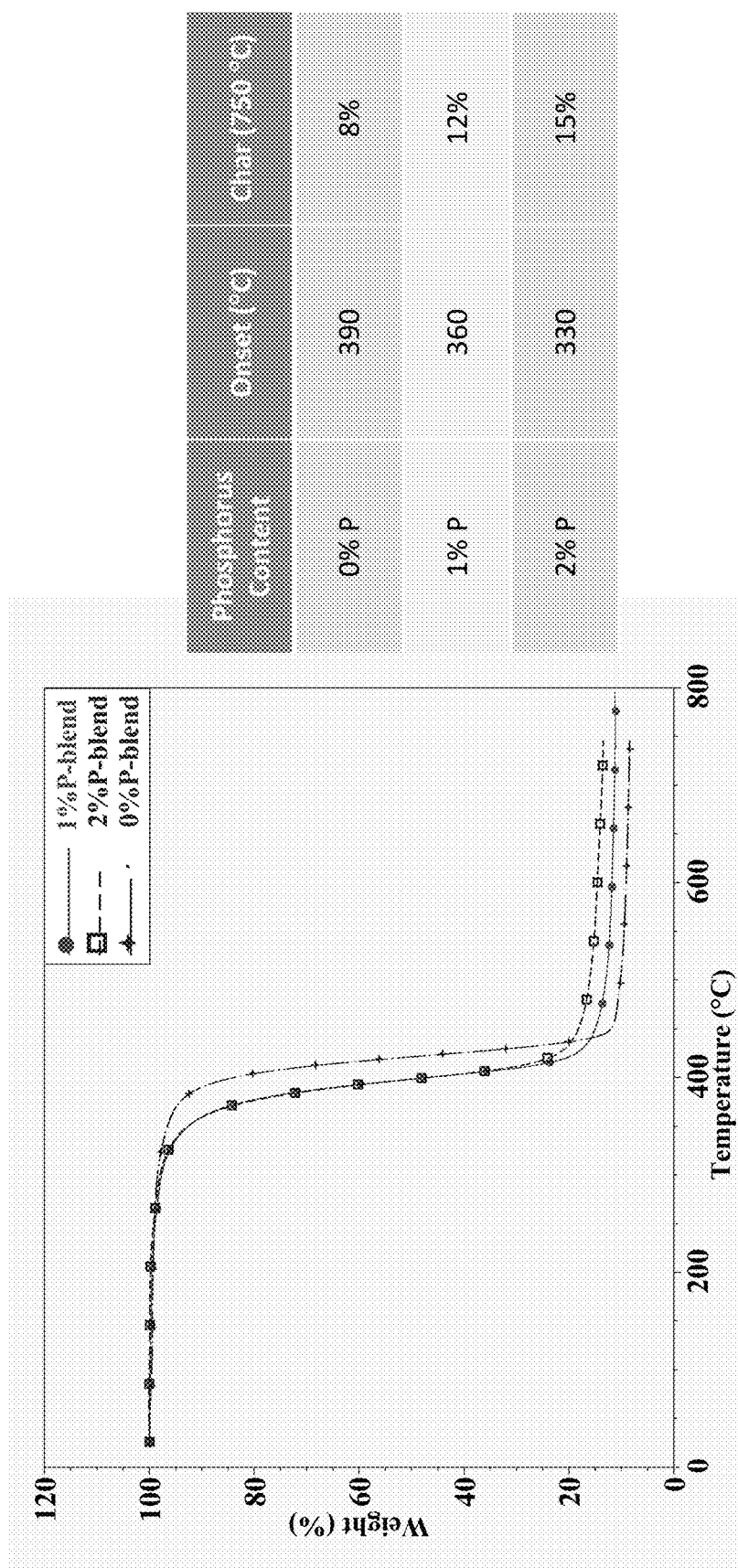
FIG. 13 shows thermal decomposition of DGEBA epoxy containing DPPH.
Figure 14:
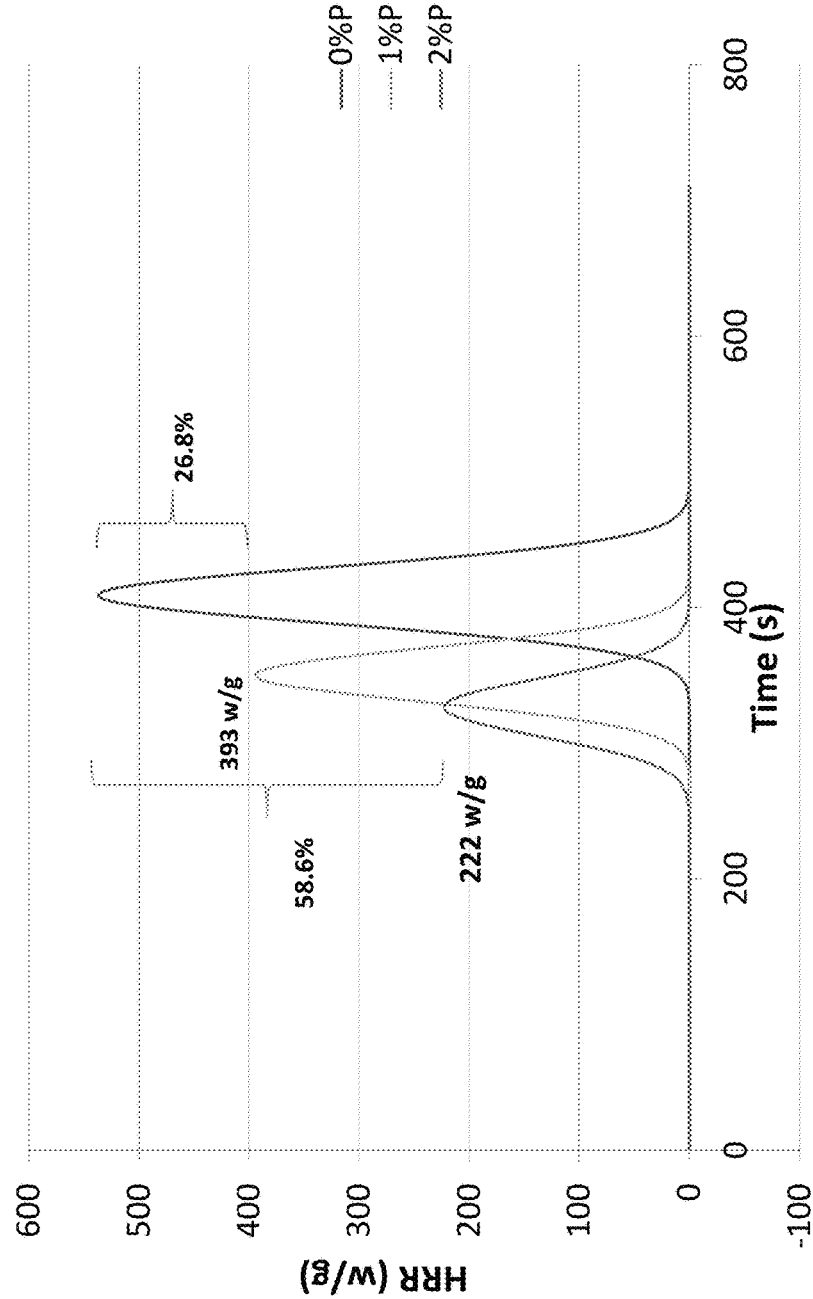
FIG. 14 shows peak heat release rate for DGEBA epoxy containing DPPD.
Figure 15:
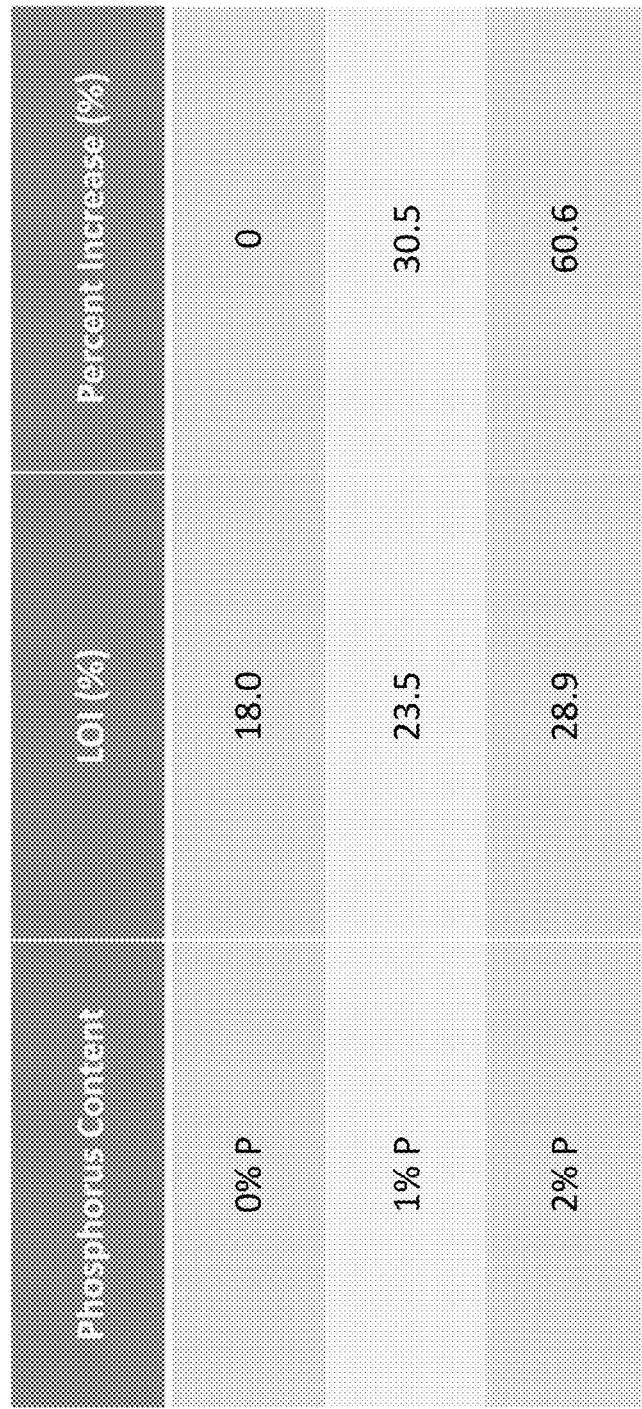
FIG. 15 shows limiting oxygen index for DGEBA epoxy samples containing DPPD.
Figure 16:
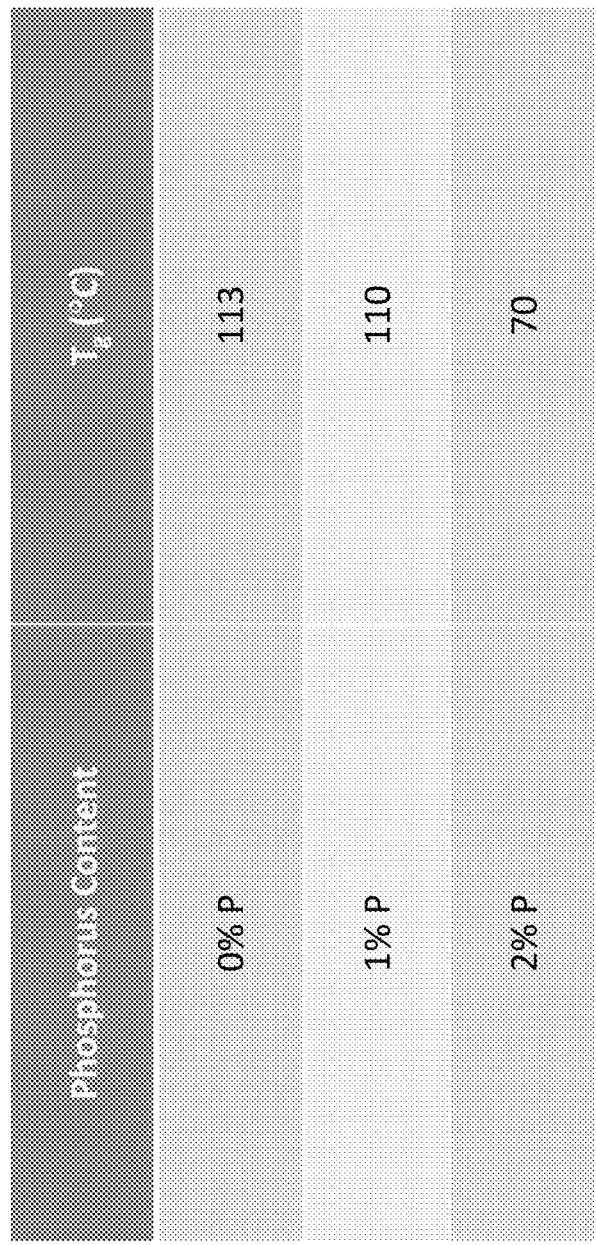
FIG. 16 shows glass transition temperatures for DGEBA epoxy containing DPPA.
Figure 17:
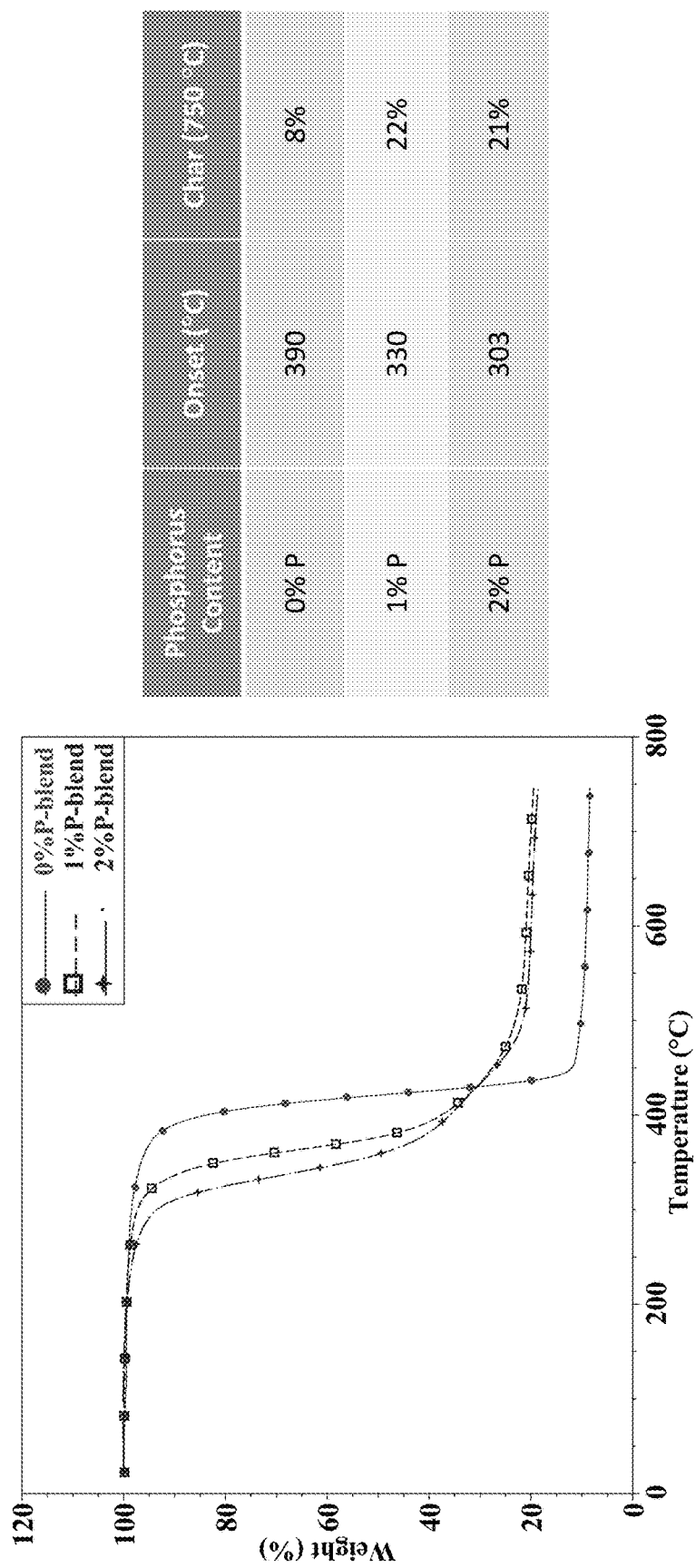
FIG. 17 shows thermal decomposition of DGEBA epoxy containing DPPA.
Figure 18:
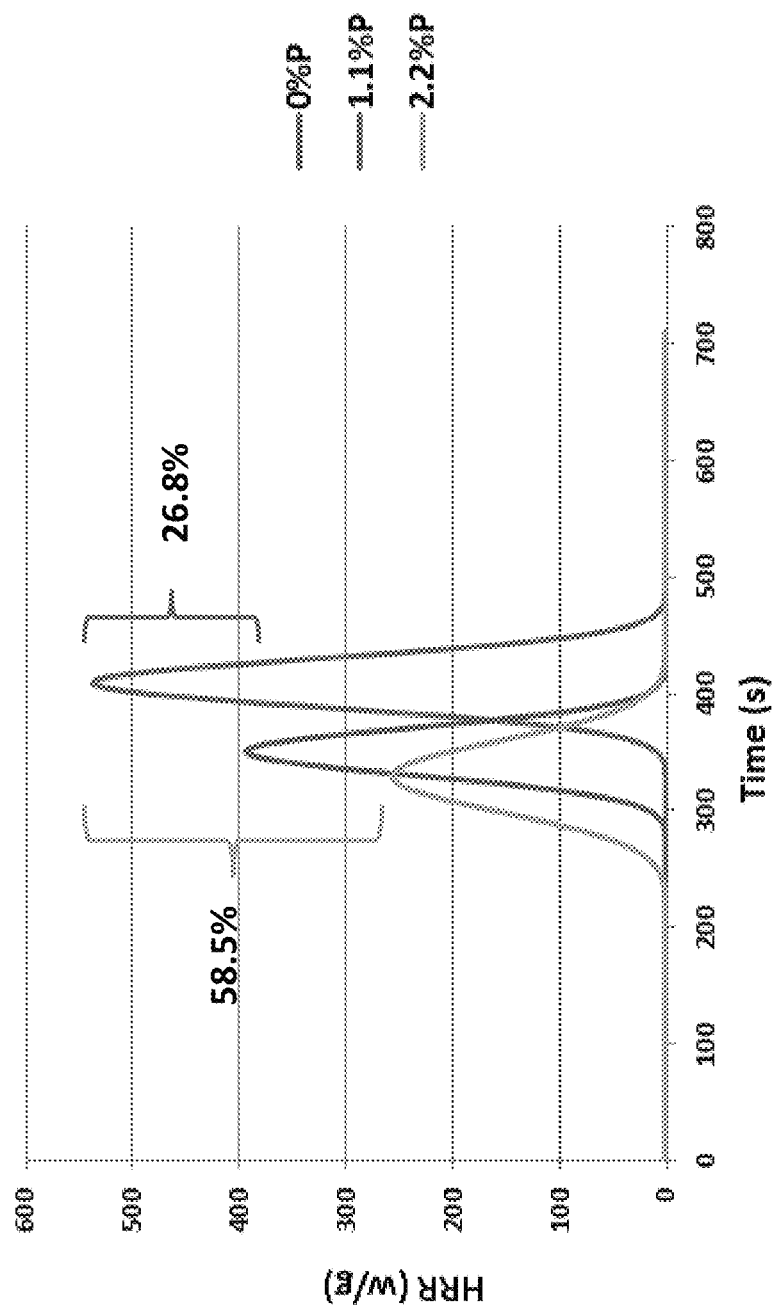
FIG. 18 shows peak heat release rate for DGEBA epoxy containing DPPA.
Figure 19:
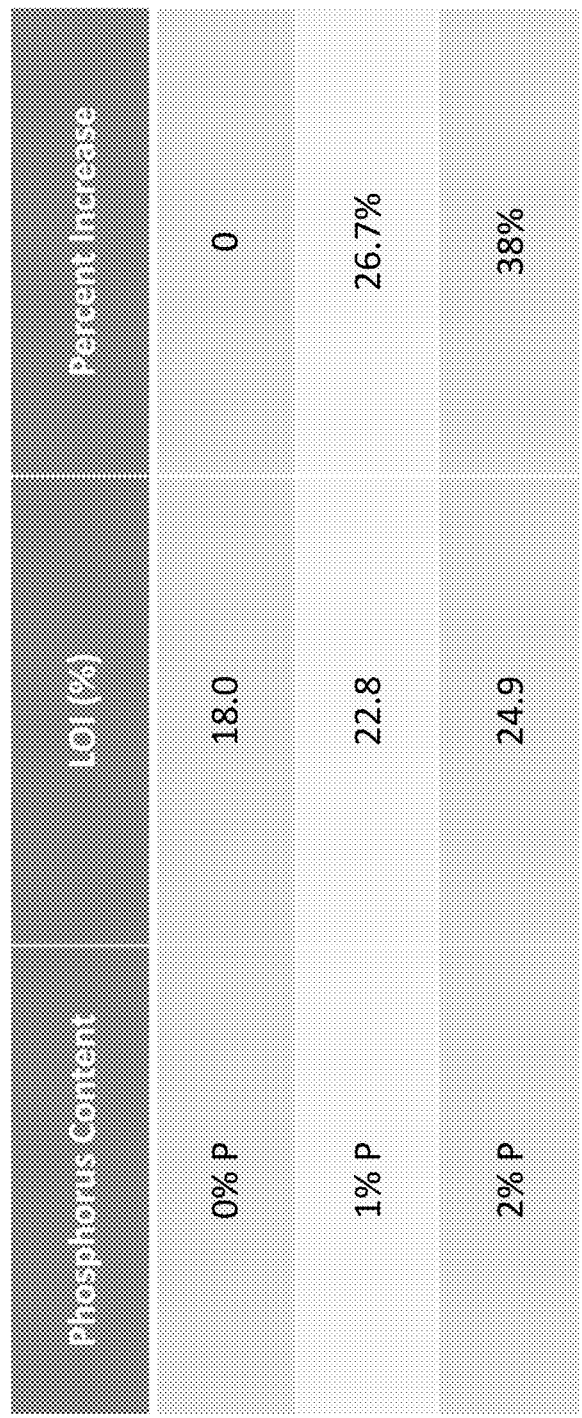
FIG. 19 shows limiting oxygen index for DGEBA epoxy containing DPPA.

Spectra detailing the degradation of DPPD are contained in FIG. 7. Although the decomposition reaction is slower for this compound, it would appear to follow the same path. The primary reaction is again the elimination of a phosphorus acid.

It is interesting that the phosphates (DPPE, DPPA) undergo more facile elimination of acid than does the phosphonate (DPPD) or the phosphinate (DPPI). Without wishing to be bound by theory, this could be due to less flexibility in the six-membered activated complex for elimination (Scheme 6).

Example 6

Flammability Ratings

Figure 20:
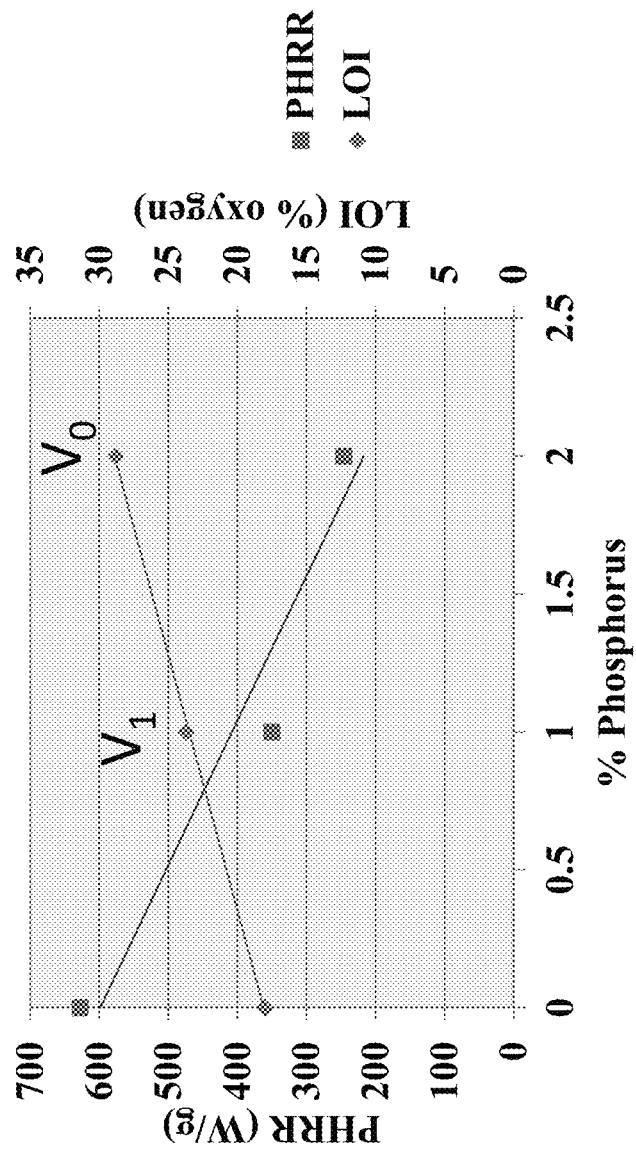
FIG. 20 shows flammability ratings for DGEBA epoxy containing DPPD.
Figure 21:
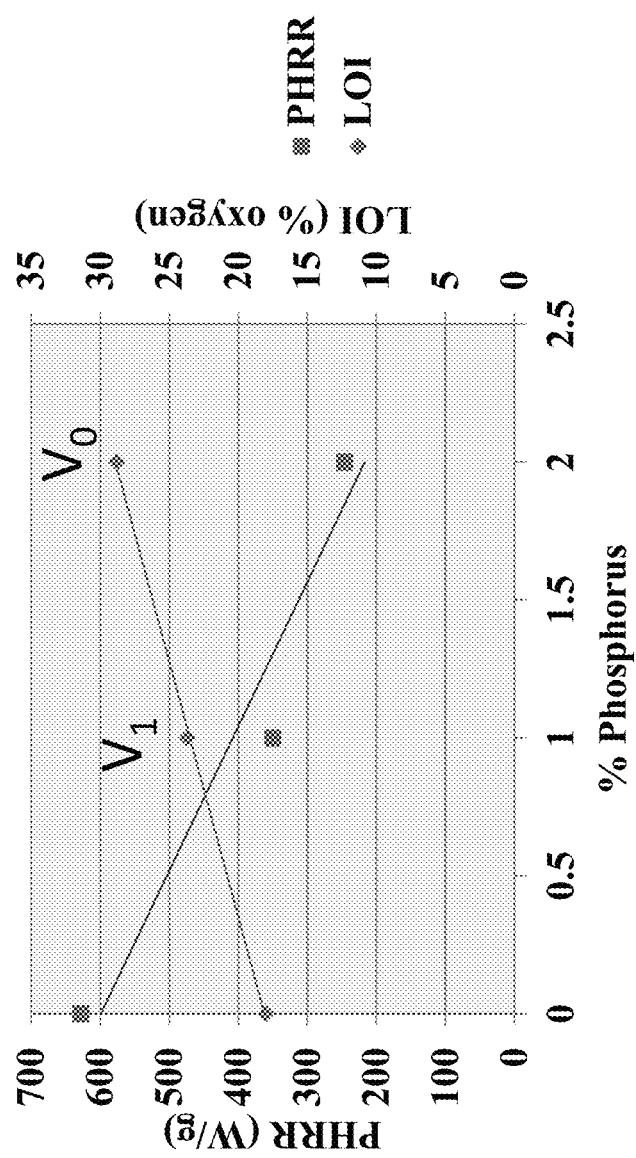
FIG. 21 shows flammability ratings for DGEBA epoxy containing DPPA.
Figure 22:
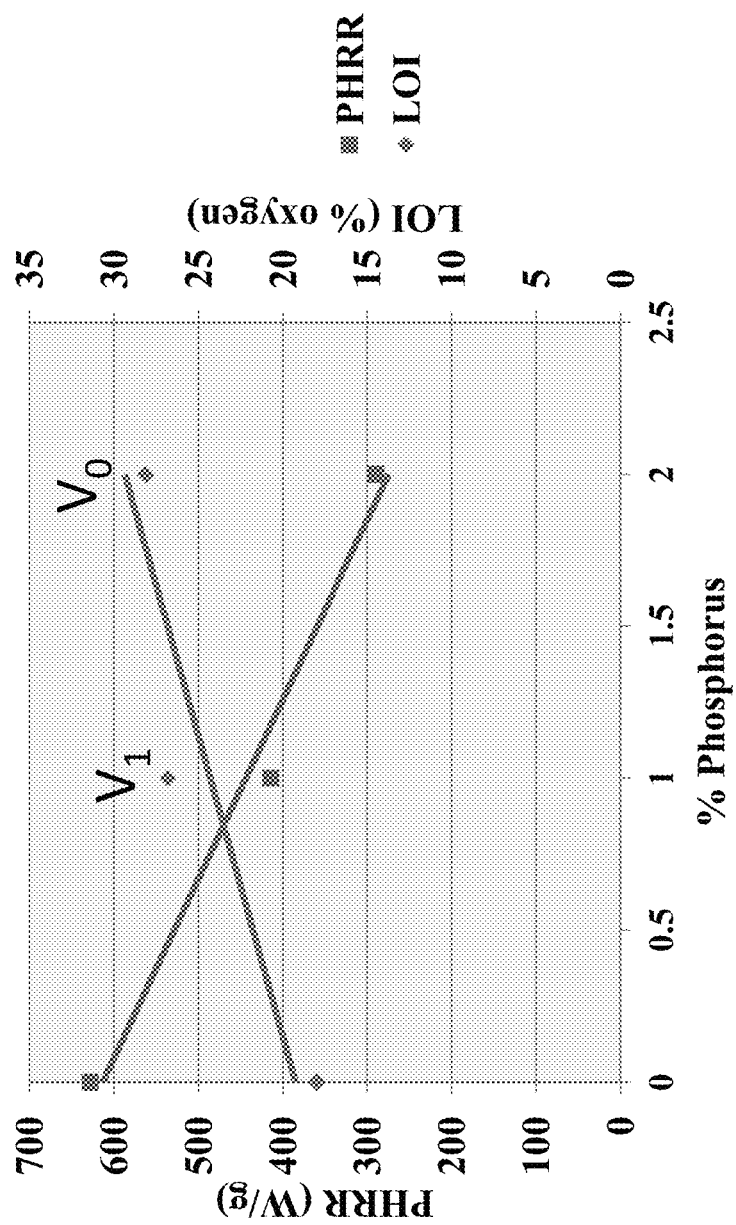
FIG. 22 shows flammability ratings for DGEBA epoxy containing DPPI.

The effectiveness DPPA, DPPD and DPPI as flame retardants was evaluated in DGEBA epoxy resin using standard techniques: pyrolysis combustion flow calorimetry (PCFC) [ASTM procedure D7309-07a], limiting oxygen index (LOI) [ASTM procedure D2863-13] and the UL 94 vertical burn test [ASTM procedure D3801-06]. Data for three representative compounds are shown in FIGS. 20-22. It may be noted that in all cases the peak heat release rate decreases smoothly and the limiting oxygen index values increase in the same way as a function of phosphorus loading. Further, a V0 rating in the UL94 test is achieved with a loading of 2% phosphorus. These and similar compounds from this and

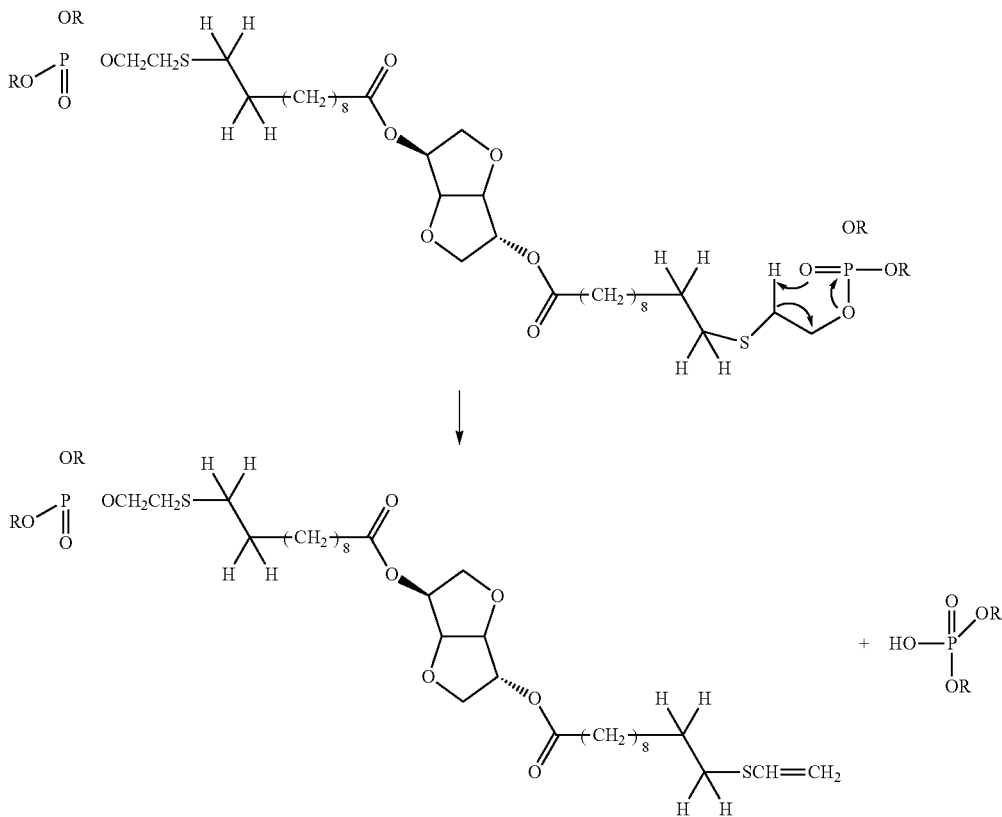

Scheme 6. Mode of Elimination of Phosphorus Acids from the Corresponding Esters.

Example 5

Properties of Phosphorus-Containing Compounds

The limiting oxygen index (LOI) values of certain phosphorus containing compounds were determined using an Oxygen Index unit from Fire Testing Technology, Ltd. and a standard method, ASTM D2863-13. Pyrolysis Combustion Flow calorimetry (PCFC) was carried out using a microscale combustion calorimeter from Fire Testing Technology, Ltd. and ASTM D7309-11.

Results for these tests are shown in FIGS. 12-19.

other series are very effective flame retardants. It should be noted that flame retardancy is achieved without significant depression of the glass transition temperature (Tg) for the polymer.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A compound according to Formula (I):

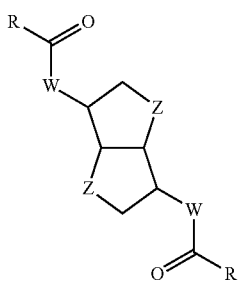

wherein
each Z is independently selected from O, NH and S;
each W is independently selected from O and NH;
each R is -A-X;
each A is independently an alkylene chain which may be substituted or interrupted by one or more heteroatoms selected from O, N, and S;
each X is independently selected from —S(CR1R2)m-Y, —S(O)(CR1R2)m-Y, —S(O)2(CR1R2)m-Y, and —Y;
Y is selected from —P(O)(R3)2, —P(O)(OR4)2, —P(O)(OR4)R3; —OP(O)(R3)2, —OP(O)(OR4)2, —OP(O)(OR4)R3 or

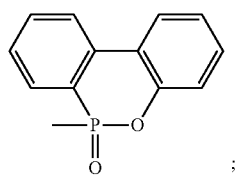 [SMILES: CP1(=O)Oc2ccccc2-c2ccccc21]

each R1 and R2 is independently selected from the group consisting of H, hydroxyl, and halogen;
each R3 and R4 is independently selected from C1-10 alkyl or aryl; and
m is an integer from 1 to 10.

2. A compound according to claim 1, wherein A contains from 2 to 20 member atoms.

3. A compound according claim 1, wherein A contains 1-5 heteroatoms.

4. A compound according to claim 1, wherein -A-X is $(CR^1R^2)_n$—X, wherein each $R^1$ and $R^2$ is independently selected from the group consisting of H, hydroxyl, and halogen and n is an integer from 2 to 20.

5. A compound according to claim 4, wherein n is an integer 2 to 10.

6. A compound according to claim 4, wherein n is an integer from 4 to 8.

7. A compound according to claim 1, wherein at least one of $R^1$ and/or $R^2$ is Br or Cl.

8. A compound according to claim 1, wherein Z is O.

9. A compound according to claim 1, wherein W is O.

10. A compound according to claim 1, wherein $R^3$ and/or $R^4$ is $C_{1-4}$ alkyl.

11. A compound according to claim 1, wherein m is 1 to 2.

12. A compound according to claim 1 selected from

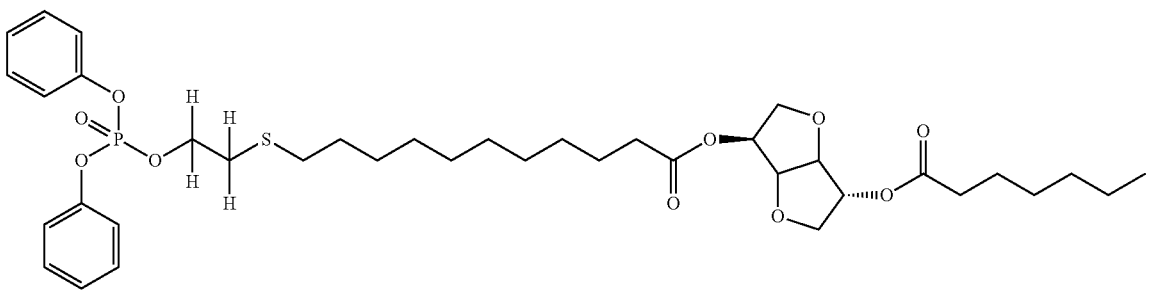

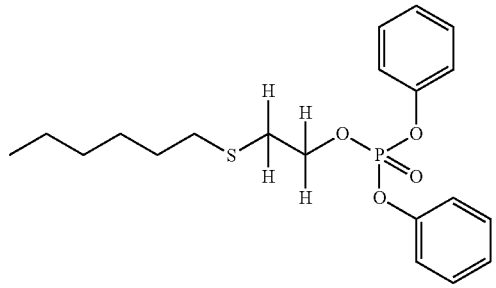

Isosorbide Di[14-(diphenylphosphato)-12-thiatetradecanoate] [DPPA]

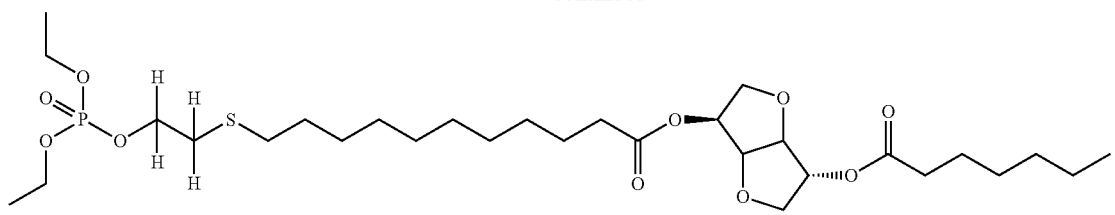
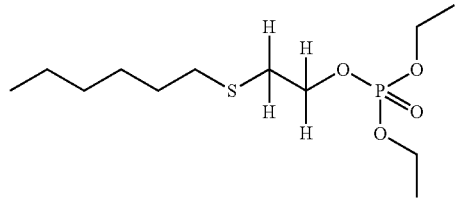
Isosorbide Di[14-(diphenylphosphato)-12-thiatetradecanoate] [DPPE]
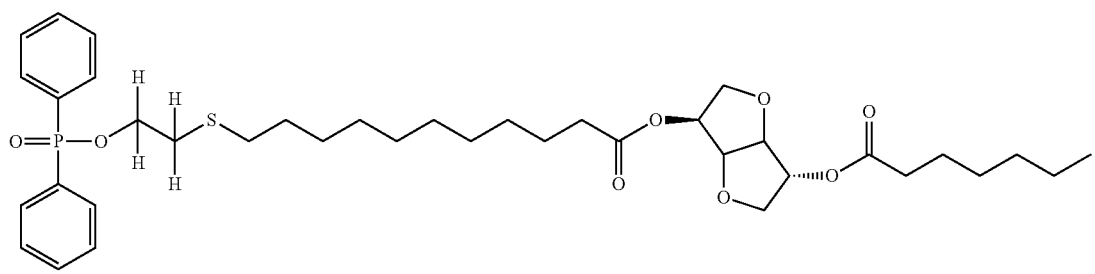
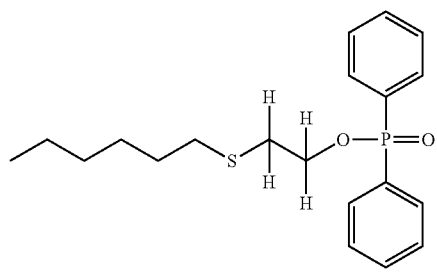
Isosorbide Di[14-(diphosphinato)-12-thiatetradecanoate] [DPPI]
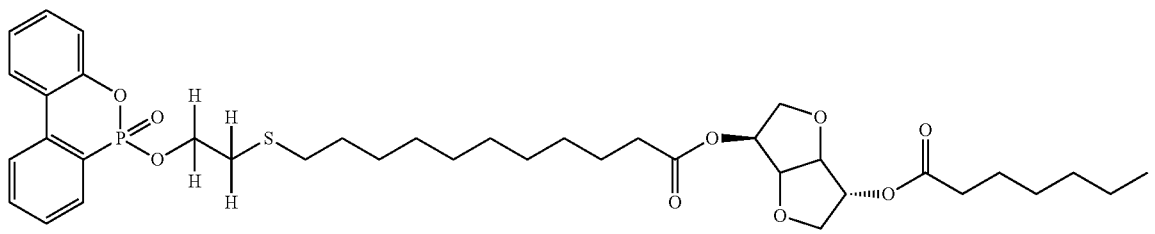
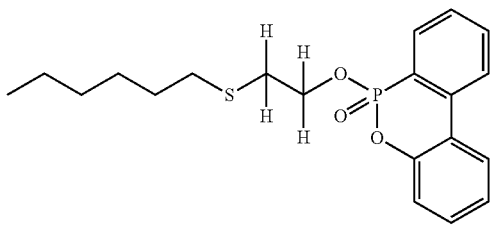
Isosorbide Di(14-dopyl-12-thiatetradecanoate) [DPPD]

13. A polymer product comprising a compound according to claim 1.

14. A polymer product according to claim 13, wherein the compound is present in about 10% to about 50% by weight.

15. A polymer product according to claim 13, wherein the compound is present in an amount sufficient to provide a phosphorus loading of about 0.01% to about 5%.

16. A polymer product according to claim 13, wherein the compound is present in an amount sufficient to provide a phosphorus loading of about 1% to about 3%.

17. A method of increasing the thermal stability of a polymer comprising adding the compound according to claim 1 to the polymer.

18. A method of increasing the maximum thermal decomposition temperature of a polymer comprising adding a compound according to claim 1 to the polymer to form a modified polymer.

19. A method according to claim 18, wherein the thermal decomposition temperature of the modified polymer is above about 300° C.

\* \* \* \* \*